United States Patent [19]

Takahashi et al.

[11] Patent Number: 4,988,456

[45] Date of Patent: Jan. 29, 1991

[54] PROCESS FOR PRODUCING W/O/W TYPE MULTIPLE EMULSION FOR MEDICINES

[75] Inventors: Yasuyuki Takahashi; Toshiro Yoshida; Takeshi Takahashi, all of Tokyo, Japan

[73] Assignee: Meiji Milk Products Company Limited, Tokyo, Japan

[21] Appl. No.: 376,943

[22] Filed: Jul. 10, 1989

Related U.S. Application Data

[63] Continuation of Ser. No. 795,357, filed as PCT JP85/00143 on Mar. 25, 1985, published as WO85/04346 on Oct. 10, 1985, abandoned.

[30] Foreign Application Priority Data

Mar. 26, 1984 [JP] Japan .................................. 59-056324
Mar. 25, 1985 [WO] PCT Int'l Appl. .... PCT/JP85/00143

[51] Int. Cl.$^5$ ....................... B01J 13/00; A61K 31/20
[52] U.S. Cl. .................... 252/314; 252/312; 424/70; 426/602; 514/558; 514/938; 514/844
[58] Field of Search .......................... 424/168, 170, 70; 514/558, 880, 844–848, 938; 252/312, 314; 426/602

[56] References Cited

U.S. PATENT DOCUMENTS

| | | |
|---|---|---|
| 2,785,978 | 3/1957 | Gracht . |
| 3,399,263 | 8/1968 | Strazdins et al. ................. 424/87 X |
| 4,328,149 | 5/1982 | Morse et al. ..................... 524/801 X |
| 4,454,113 | 6/1984 | Hemker ............................... 252/312 |
| 4,590,086 | 5/1986 | Takahashi et al. .................... 426/602 |
| 4,626,443 | 12/1986 | Takahashi et al. .................... 426/602 |
| 4,626,444 | 12/1986 | Takahashi et al. .................... 426/602 |
| 4,632,840 | 12/1986 | Takahashi et al. .................... 426/602 |
| 4,650,690 | 3/1987 | Bams et al. . |
| 4,931,210 | 6/1990 | Takahashi et al. .................... 252/314 |

FOREIGN PATENT DOCUMENTS

| | | |
|---|---|---|
| 8215829 | 1/1982 | Japan . |
| 58-175475 | 10/1983 | Japan . |
| 60-120960 | 6/1985 | Japan . |
| 1235667 | 6/1971 | United Kingdom . |
| 2143839 | 3/1986 | United Kingdom . |

OTHER PUBLICATIONS

Chemical Abstracts, vol. 87, No. 7, Aug. 15, 1977.

*Primary Examiner*—John S. Maples
*Attorney, Agent, or Firm*—Browdy and Neimark

[57] ABSTRACT

The present invention relates to a process for producing a W/O/W type multiple emulsion using a polyglycerol polyricinolate (i.e. a polyglycerol ester of a polycondensed fatty acid of caster oil).

The use of the polyglycerol polyricinolate is effective in increasing the rate of formation of the W/O/W type multiple emulsion remarkably and giving a W/O/W type multiple emulsion which is stable over a long period of time. The W/O/W type multiple emulsion has also an excellent heat stability and is useful for the production of medicines and cosmetics.

3 Claims, 1 Drawing Sheet

PROCESS FOR PRODUCING W/O/W TYPE MULTIPLE EMULSION FOR MEDICINES

This application is a continuation of application Ser. No. 06/795,357, filed as PCT JP85/00143 on Mar. 25, 1985, published as WO85/04346 on Oct. 10, 1985, now abandoned.

FIELD OF THE ART

The present invention relates to a process for producing a very fine W/O/W type multiple emulsion having an excellent stability.

More particularly, the present invention relates to a process for producing a W/O/W type multiple emulsion having an excellent heat stability for the production of medicines, cosmetics, etc. other than food.

An object of the present invention is to produce a W/O/W type multiple emulsion useful for the production of various products in the form of an emulsion, such as medicines and cosmetics.

BACKGROUND OF THE ART

The use of W/O/W type multiple emulsions for various purposes such as the production of cosmetics, medicines, food and drinks is expected, since generally they have a very fine texture and a smooth touch upon application to the skin and a water-soluble substance can be incorporated in fat globules and the apparent fat content thereof can be increased.

In conventional processes for preparing the W/O/W type multiple emulsion, a Span (Trade Mark) emulsifier such as sorbitan monooleate is used in an amount of at least 20% based on an oil in the primary emulsification and then the second emulsification is effected.

However, even when such a large amount of the emulsifying agent is used, the multiple-phase emulsion state is broken or the emulsification rate is reduced by heating effected in the final stage for sterilization or the like. This is a serious demerit.

DISCLOSURE OF THE INVENTION

The inventors have now succeeded in producing an excellent W/O/W type multiple emulsion by using a polyglycerol polyricinolate (i.e. a polyglycerol ester of a polycondensed fatty acid of castor oil) as an emulsifier.

According to the present invention, the intended effects can be obtained with only a small amount of the polyglycerol polyricinolate used as the emulsifier and the obtained W/O/W type multiple emulsion has an excellent heat stability, freeze resistance and storage stability. The inner aqueous phase is capable of containing a large amount of effective ingredients. Since this phase is very fine, it can be formed with a high formation rate and is stable to physical treatments.

Figure 1:
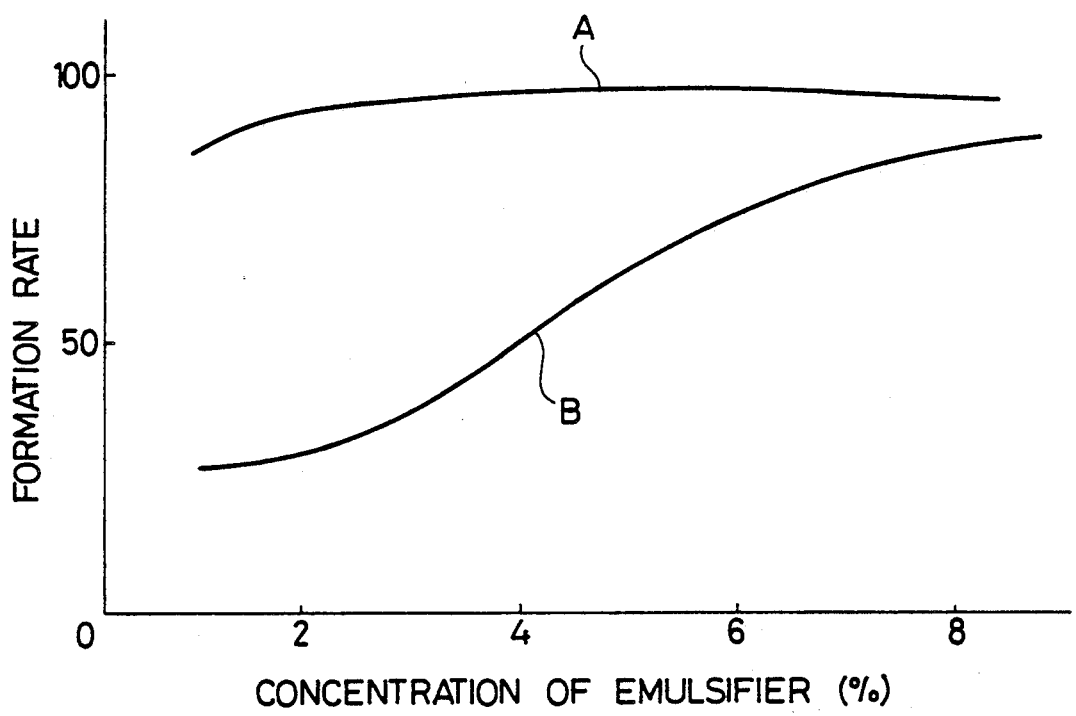
FIG. 1 shows changes in the formation rate of the W/O/W type multiple emulsion with the concentration of the emulsifiers determined in Test Example 5.

The polyglycerol polyricinolates used in the present invention are represented by the following formula (I):

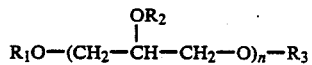

wherein n represents a number of 2 to 12 and $R_1$, $R_2$ and $R_3$ each represent a hydrogen atom or a polyricinoleic acid of the following formula (II):

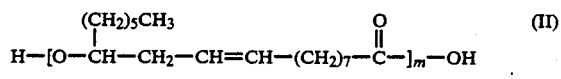

in which m represents a number of 2 to 10.

The polyglycerol polyricinolates of the above formula may be used either solely or in the form of a suitable mixture of two or more of them in the present invention.

The polyglycerol polyricinolate (hereinafter referred to as "the emulsifier") may be incorporated in the aqueous phase, oil phase or both of them. It is unnecessary to dissolve the former in the latter and they may be in the form of a suspension when the emulsification is initiated. The amount of the emulsifier is about 0.1 to 20%, preferably 1 to 15% and particularly 1 to 10%, based on the oil used. If necessary, other emulsifiers may also be used suitably. Though these emulsifiers are not particularly limited, preferred examples of them include lecitin and/or fatty acid diesters of glycerol.

The oily substances are not limited. Examples of them include beeswax, lanolin, vaseline, paraffin, animal oils and vegetable oils. When a hardened oil is used, it should be molten by heating.

Water used in addition to the above-mentioned components may contain protein, starch, gum, emulsifier, phosphoric acid or its salt, organic acid or its salt, colorant, seasoning and medicine to form an aqueous phase and it may be kept heated.

In an embodiment of the process of the present invention for producing the W/O/W type multiple emulsion, an aqueous phase containing an emulsifier is added gradually to an oil phase containing an emulsifier and the W/O emulsion thus obtained is inverted into a W/O/W type multiple emulsion at once.

In another embodiment of the process of the present invention, a W/O emulsion is prepared first by either of the following two methods. The first method comprises adding an aqueous phase gradually to an oil phase containing an emulsifier to form a W/O emulsion directly, while the second method comprises adding an oil phase containing an emulsifier to an aqueous phase to form an O/W emulsion and then agitating the emulsion to invert the same into a W/O emulsion. The second method, i.e. a phase inversion process wherein fine, uniform droplets can be formed is preferred, though the W/O emulsion comprising fine droplets can be obtained by both methods.

In this second process, an oily substance containing the emulsifier is added slowly to the aqueous phase under agitating.

To obtain a fine emulsion, it is not recommended to mix large amounts of the aqueous and non-aqueous phase at once. Though the amounts of the oily substance and water are determined suitably depending on the purpose, a ratio of the oily substance to water of about 3:1 to 1:3 is preferred from the viewpoint of the subsequent phase inversion.

The O/W emulsion thus obtained is agitated thoroughly with a homomixer to invert it into a W/O emulsion which is very fine and smooth. Further, medicines and various additives can be enclosed in the aqueous phase dispersed in the oil phase. The agitating with the homomixer is effected preferably vigorously at a rate of, for example, about 3000 to 8000 rpm. An emulsifying device such as a homogenizer or a stirring device such as a Votator may also be used. To facilitate the subsequent emulsification, the W/O emulsion is preferably heated to 50° to 80° C.

The aqueous phase is prepared as follows according to the present invention. The following additive(s) is-(are) added to water:

casein, sodium caseinate, gelatin, wheat protein, starch, modified starch, soybean protein, plasma protein, whey protein, egg white, egg yolk, dextrin, cyclodextrin, starch derivatives, locust bean gum, xanthane gum, pullulan, dextran, curdlan, guar gum, tamarind gum, agar, carrageenan, furcellaran, alginic acid and salts thereof, propylene glycol alginate, pectin, arabinogalactan, crystalline cellulose, CMC, methylcellulose, acacia gum, tragacanth gum, Karaya gum, polysodium acrylate, orthophosphoric acid, pyrophosphoric acid, polyphosphoric acid and salts of these phosphoric acids, common salt, vinegar, organic acids and salts of them, emulsifiers and mixtures of these additives. The emulsifiers used herein include sucrose fatty acid esters, polyoxyethylene sorbitan fatty acid esters, Pluronic emulsifier and Tetronic emulsifier. In addition, colorants and seasonings may also be incorporated in the aqueous phase according to the purpose. It is preferred to heat the aqueous phase to a temperature of about 50° to 80° C. to facilitate the subsequent emulsification. Though the order of the addition is not limited, generally the W/O emulion is first placed in the agitator and the aqueous phase containing the emulsifiers, etc. is added thereto to perform the operation in an advantageous manner. The agitator is not limited. The agitators usable in this process include those having agitating blades arranged near the bottom, suction type agitators having agitating blades extending all over the inside thereof, agitators of mere suction mixing type, homomixers, homogenizers and Votators. A preferred agitator is one in which an impact applied to the upper W/O emulsion layer is weak and a stable W/O/W type multiple emulsion can be prepared.

The aqueous phase is mixed with the above-mentioned W/O emulsion and the mixture is agitated with the agitator at, for example, 250 rpm for 5 min. and then treated with a homogenizer to obtain the intended W/O/W emulsion having a very fine texture.

Thus, according to the present invention, a stable W/O/W type multiple emulsion comprising extremely fine droplets can be obtained and this emulsion can be used in the preparation of cosmetics and medicines for external and internal uses.

The cosmetics which can be prepared by using said W/O/W type multiple emulsion include creams such as emolient cream, cleaning cream, foundation cream, massage cream, nutrient cream, hand cream and hair cream; and lotions such as emolient lotion, cleansing lotion, aftershaving lotion, suntan lotion, hand lotion and hair treatment lotion.

The medicines for external use include salves, poultices, medicines for burn, etc.

The medicines for internal use include internal medicines, injections and suppositories.

TEST 1

1%, based on the oil, of a polyglycerol polyricinolate having a degree of polymerization of glycerol and a degree of condensation of ricinoleic acid as shown in Table 1 was added as an emulsifier to 300 g of hardened soybean oil at 50° C. and mixed.

The mixture was added successively to 200 g of water at 50° C. to obtain an O/W emulsion, which was agitated with a homomixer at 6000 rpm to effect the phase inversion. Thus, a W/O emulsion was obtained.

500 g of water containing 1% of sodium caseinate and 2% of sorbitan monostearate was heated to 70° C. The W/O emulsion heated to 70° C. was added thereto and the mixture was agitated in an agitator having agitating blades arranged at the bottom thereof at 250 rpm for 5 min. The mixture was further treated in a homogenizer at 100 kg/cm² and cooled to 5° C.

The W/O/W type multiple emulsion formation rate was examined to obtain the results shown in Table 1.

The W/O/W type multiple emulsion formation rate was determined according to a method of Matsumoto et al., described in "Yukagaku" 26 (10), 655 (1977).

TABLE 1

| Degree of polymerization of glycerol (n) | Degree of condensation of ricinoleic acid (m) | | | | |
|---|---|---|---|---|---|
| | 2 | 3 | 4 | 5 | 6 |
| 2 | 70% | 72% | 72% | 74% | 75% |
| 3 | 75 | 76 | 76 | 77 | 78 |
| 4 | 87 | 93 | 95 | 95 | 94 |
| 5 | 85 | 90 | 94 | 95 | 94 |
| 6 | 88 | 89 | 93 | 95 | 94 |

The figures represent the formation rate.

Symbols n and m in Table 1 are as defined in the above formulae (I) and (II).

TEST 2

Varieties of emulsifiers for the outer aqueous phase

The same procedure as in Test 1 was repeated except that 1%, based on the oil, of a polyglycerol polyricinolate having a degree of polymerization of glycerol of 4 and a degree of condensation of ricinoleic acid of 5 was used and that the emulsifier was replaced with another emulsifier which was added in an amount of 2% based on the outer aqueous phase to obtain a W/O/W type multiple emulsion. The formation rate of the W/O/W type multiple emulsion was examined to obtain the results shown in Table 2.

The W/O/W type multiple emulsion formation rate was determined in the same manner as in Test 1.

TABLE 2

| Emulsifier | Formation rate |
|---|---|
| sugar ester (HLB 15.0) | 95 |
| sugar ester (HLB 13.0) | 95 |
| sugar ester (HLB 11.0) | 95 |
| sugar ester (HLB 9.5) | 94 |
| sugar ester (HLB 8.0) | 91 |
| sugar ester (HLB 6.0) | 87 |
| sugar ester (HLB 2.0) | 82 |
| sugar ester (HLB 1.0) | 75 |
| sorbitan monostearate | 90 |
| sorbitan tristearate | 82 |
| propylene glycol monostearate | 90 |
| glycerol monostearate | 83 |
| glycerol distearate | 73 |
| diglycerol monostearate | 87 |
| tetraglycerol monostearate | 90 |
| octaglycerol monostearate | 90 |
| decaglycerol monostearate | 92 |
| polyoxyethylene (20) sorbitan monostearate | 92 |
| citric monoglyceride (monostearate) | 88 |
| acetic monoglyceride (monostearate) | 85 |
| succinic monoglyceride (monostearate) | 86 |

TABLE 2-continued

| Emulsifier | Formation rate |
|---|---|
| lactic monoglyceride (monostearate) | 85 |
| diacetyltartaric monoglyceride (monostearate) | 87 |
| lecithin | 90 |

TEST 3

The same procedure as in Test 1 was repeated using various polyglycerol polyricinolates and emulsifiers for the outer aqueous phase. In this test, 1%, based on the oil, of the polyglycerol polyricinolate and 2%, based on the outer aqueous phase, of the emulsifier were used and the W/O/W type multiple emulsion formation rate was determined to obtain the results shown in Table 3.

The W/O/W type multiple emulsion formation rate was determined in the same manner as in Test 1.

TABLE 3

| Emulsifier for outer aqueous phase | Degree of polymerization of glycerol (n) | Formation rate (%) Polyglycerol polyricinolate Degree of condensation of ricinoleic acid (m) | | | | |
|---|---|---|---|---|---|---|
| | | 2 | 3 | 4 | 5 | 6 |
| Sugar ester (HLB13.0) | 2 | 70 | 73 | 72 | 74 | 74 |
| | 3 | 76 | 76 | 77 | 77 | 77 |
| | 4 | 85 | 92 | 95 | 95 | 94 |
| | 5 | 86 | 91 | 94 | 95 | 95 |
| | 6 | 86 | 91 | 95 | 94 | 94 |
| Sugar ester (HLB 8.0) | 2 | 67 | 70 | 70 | 70 | 71 |
| | 3 | 72 | 73 | 73 | 73 | 74 |
| | 4 | 83 | 89 | 90 | 91 | 92 |
| | 5 | 84 | 88 | 91 | 92 | 91 |
| | 6 | 82 | 88 | 91 | 92 | 92 |
| Sugar ester (HLB 2.0) | 2 | 62 | 63 | 63 | 64 | 65 |
| | 3 | 68 | 69 | 70 | 70 | 71 |
| | 4 | 80 | 80 | 82 | 82 | 81 |
| | 5 | 80 | 81 | 82 | 82 | 82 |
| | 6 | 81 | 81 | 81 | 82 | 81 |
| Sorbitan monostearate | 2 | 70 | 70 | 72 | 71 | 72 |
| | 3 | 73 | 73 | 76 | 75 | 75 |
| | 4 | 82 | 87 | 90 | 90 | 90 |
| | 5 | 81 | 87 | 90 | 90 | 89 |
| | 6 | 81 | 87 | 89 | 90 | 89 |
| Glycerol monostearate | 2 | 64 | 64 | 65 | 66 | 67 |
| | 3 | 65 | 69 | 69 | 71 | 71 |
| | 4 | 80 | 81 | 83 | 83 | 83 |
| | 5 | 80 | 81 | 82 | 83 | 83 |
| | 6 | 81 | 82 | 82 | 83 | 82 |
| Polyoxyethylene (20) sorbitan monostearate | 2 | 70 | 73 | 73 | 73 | 75 |
| | 3 | 73 | 74 | 76 | 76 | 76 |
| | 4 | 84 | 89 | 92 | 92 | 92 |
| | 5 | 85 | 90 | 92 | 91 | 92 |
| | 6 | 85 | 89 | 92 | 92 | 92 |
| Lecithin | 2 | 69 | 72 | 71 | 72 | 74 |
| | 3 | 74 | 74 | 76 | 77 | 77 |
| | 4 | 83 | 87 | 90 | 90 | 90 |
| | 5 | 84 | 88 | 90 | 91 | 91 |
| | 6 | 84 | 87 | 89 | 90 | 91 |

TEST 4

The same procedure as in Test 1 was repeated except that the polyglycerol ricinolate used in Test 1 was replaced with 1%, based on the oil, of a mono- or polyglycerol ricinolate and that the degree of polymerization of glycerol and the degree of esterification of ricinoleic acid were altered. The results are shown in Table 4.

TABLE 4

| Degree of polymerization of glycerol | Degree of esterification of ricinoleic acid | | | |
|---|---|---|---|---|
| | 1 | 2 | 3 | 6 |
| 1 | 17% | 19% | 0% | —% |
| 2 | 20 | 18 | 12 | — |
| 3 | 23 | 28 | 25 | — |
| 6 | 20 | 28 | 35 | 43 |
| 10 | 18 | 27 | 35 | 42 |

The figures represent the formation rate.

In the following Tests 5 to 7 and examples of the present invention, the polyglycerol polyricinolate used was a mixture of esters having a degree of polymerization of glycerol of 3 to 4 and a degree of condensation of ricinoleic acid of 4 to 5.

TEST 5

0.5 to 10% (various), based on the oil, of a polyglycerol polyricinolate or sorbitan monooleate (Span 80) was added to 300 g of hardened soybean oil heated to 50° C. and mixed.

The mixture was added slowly to 200 g of water heated to 50° C. to obtain an O/W emulsion, which was agitated with a homomixer at 6000 rpm to effect the phase inversion. Thus, a W/O emulsion was obtained.

500 g of water containing 1% of sodium caseinate and 2% of sorbitan monostearate was heated to 70° C. The W/O emulsion obtained above was heated to 70° C. and added thereto and the obtained mixture was agitated in an agitator having agitating blades arranged at the bottom thereof at 250 rpm for 5 min. The mixture was further treated in a homogenizer at 100 kg/cm$^2$ and cooled to 5° C.

The W/O/W type multiple emulsion formation rate was examined to obtain the results shown in FIG. 1 wherein a curve A shows the results obtained when polyglycerol polyricinolate was used and a curve B shows those obtained when Span 80 was used.

It is apparent from FIG. 1 that the polyglycerol polyricinolates are quite effective in the production of the W/O/W type multiple emulsion.

The W/O/W type multiple emulsion formation rate was determined according to a method of Matsumoto et al., described in "Yukagaku" 26 (10), 655 (1977).

TEST 6

W/O/W type multiple emulsions were produced in the same manner as in Test 5 except the following points to examine the average droplet diameter and W/O/W formation rate.

A: The same procedure as in Test 5 was repeated except that 1.0%, based on the oil, of the polyglycerol polyricinolate was used.

B: The same procedure as in Test 5 was repeated except that 1.0%, based on the oil, of polyglycerol polyricinolate was used and that the aqueous phase was added to the oil phase to effect the primary emulsification.

C: The polyglycerol polyricinolate used as the emulsifier was replaced with 1.0%, based on the oil, of a mixture of sorbitan monostearate and sorbitan monooleate in a ratio of 1:1.

D: 10.0%, based on the oil, of the same mixture as in item C was used.

The results are shown in Table 5.

TABLE 5

| Average droplet diameter of W/O emulsion | Formation rate (%) | | | | |
|---|---|---|---|---|---|
| | Immediately after the preparation | one week | two weeks | three weeks | four weeks |
| A  0.6 μm | 95.4 | 92.0 | 90.5 | 88.7 | 86.5 |
| B  1.0 μm | 75.5 | 73.0 | 65.5 | 62.0 | 58.0 |
| C  2.5 μm | 35.0 | 28.0 | 15.0 | 11.2 | 6.3 |
| D  1.2 μm | 82.5 | 80.1 | 75.2 | 71.4 | 65.3 |

*The emulsions were stored at 5° C.

TEST 7

The same procedure as in Test 5 was repeated except that the polyglycerol polyricinolate was replaced with 1%, based on the oil, of another emulsifier to obtain a W/O/W emulsion. The average droplet diameter and W/O/W type multiple emulsion formation rate were examined. Further, the W/O/W type multiple emulsion formation rates after storage at 5° C. for one month and after heating at 120° C. for 30 min were also examined to obtain the results shown in Table 6.

The W/O/W type multiple emulsion formation rate was determined in the same manner as in Test 5.

TABLE 6

| | Average droplet diameter | Formation rate (%) | Formation rate after storage at 5° C. for 1 month (%) | Formation rate after heating at 120° C. for 30 min (%) |
|---|---|---|---|---|
| 1 polyglycerol polyricinolate | 0.6 | 95.4 | 86.5 | 95 |
| 2 lecithin | 2.7 | 30.2 | 5.0 | 19 |
| 3 glycerol monostearate | 3.8 | 18.5 | 2.7 | 15 |
| 4 glycerol monooleate | 2.2 | 28.3 | 4.3 | 32 |
| 5 diglycerol monostearate | 4.3 | 14.1 | 3.0 | 10 |
| 6 diglycerol monooleate | 1.8 | 40.2 | 12.0 | 35 |
| 7 sorbitan tristearate | 3.3 | 17.3 | 3.5 | 11 |
| 8 sucrose fatty acid ester | 4.1 | 11.0 | 4.6 | 7 |

Example 1 Cleansing cream

| | | |
|---|---|---|
| 1. beeswax | 10 | wt. % |
| 2. lanolin | 3 | wt. % |
| 3. vaseline | 10 | wt. % |
| 4. liquid paraffin | 42 | wt. % |
| 5. polyglycerol polyricinolate | 4 | wt. % |
| 6. perfume | 0.5 | wt. % |
| 7. purified water | 30.5 | wt. % |
| | 100.0 | wt. % |

The above components 1 to 4 were heated to 50° C. The component 5 was added to the mixture and mixed.

Separately, the component 7 was heated to 50° C. and the component 6 was added thereto. The above-mentioned oily mixture was added thereto at a rate of 20 ml/min under agitating at 6000 rpm. In the course of this step, the O/W emulsion was inverted to obtain a W/O emulsion. 100 parts by weight of the W/O emulsion was dispersed in 20 parts by weight of a 10% aqueous solution of polyoxyethylene sorbitan monolaurate. The dispersion was emulsified again with a homomixer at 80° C. to obtain a cleansing cream comprising essentially the W/O/W type multiple emulsion.

The obtained cleansing cream was free of a greasy touch and realized a fresh feeling upon use. The cream had very excellent spreadability and cleansing effects and a stable emulsion state.

Example 2 Massage cream

| | | |
|---|---|---|
| 1. anhydrous lanolin | 10 | wt. % |
| 2. vaseline | 50 | wt. % |
| 3. hardened fat | 1 | wt. % |
| 4. liquid paraffin | 10 | wt. % |
| 5. perfume | 0.5 | wt. % |
| 6. polyglycerol polyricinolate | 5 | wt. % |
| 7. purified water | 23.5 | wt. % |
| | 100.0 | wt. % |

The above components 1 to 4 were heated to 50° C. The component 6 was added to the mixture and the component 5 was added thereto under agitating with a homomixer at 6000 rpm. The component 7 heated to 50° C. was added successively to the mixture to obtain a W/O emulsion.

100 parts by weight of the W/O emulsion was dispersed in 20 parts by weight of a 10% aqueous solution of polyoxyethylene sorbitan monoleate. The dispersion was emulsified again with a homomixer at 80° C. to obtain a massage cream comprising essentially the W/O/W type multiple emulsion.

Example 3 Hand cream

| | | |
|---|---|---|
| 1. beeswax | 10 | wt. % |
| 2. vaseline | 12 | wt. % |
| 3. liquid paraffin | 35 | wt. % |
| 4. solid paraffin | 10 | wt. % |
| 5. polyglycerol polyricinolate | 3 | wt. % |
| 6. purified water | 30 | wt. % |
| | 100.0 | wt. % |

The above components 1 to 5 were heated to 50° C. The component 6 heated to 50° C. was added successively to the mixture under agitating with a homomixer at 6000 rpm to obtain a W/O emulsion.

100 parts by weight of this emulsion was dispersed in 25 parts by weight of a 10% aqueous solution of polyoxyethylene sorbitan monooleate. The dispersion was emulsified again with a homomixer at 80° C. to obtain a hand cream comprising essentially the W/O/W type multiple emulsion.

Example 4 Hair cream and hair lotion

| | | |
|---|---|---|
| 1. beeswax | 2 | wt. % |
| 2. liquid paraffin | 45.5 | wt. % |
| 3. polyglycerol polyricinolate | 2.5 | wt. % |
| 4. purified water | 50 | wt. % |
| 5. perfume | a small amount | |
| | 100.0 | wt. % |

The above components 1 and 3 were heated to 50° C. The component 5 was added thereto under stirring with a homomixer at 6000 rpm and then the component 4 heated to 50° C. was added slowly to the mixture to obtain a W/O emulsion.

(1) Hair cream 100 parts by weight of the W/O emulsion was dispersed in 20 parts by weight of a 10% aqueous solution of polyoxyethylene sorbitan monolaurate. The dispersion was emulsified again with a homomixer at 80° C. to obtain a hair cream comprising essentially the W/O/W type multiple emulsion.

(2) Hair lotion 100 parts by weight of the W/O emulsion obtained as above was dispersed in 100 parts by weight of purified water containing 2% of a sorbitan monopalmitate and 2% of a polyoxyethylene monostearate. The dispersion was emulsified again with a homomixer at 80° C. to obtain a hair lotion comprising essentially the W/O/W type multiple emulsion.

| Example 5 Cleansing lotion | |
| --- | --- |
| 1. beeswax | 3.0 wt. % |
| 2. solid paraffin | 5.0 wt. % |
| 3. vaseline | 10.0 wt. % |
| 4. liquid paraffin | 30.0 wt. % |
| 5. polyglycerol polyricinolate | 6.0 wt. % |
| 6. perfume | 0.5 wt. % |
| 7. purified water | 45.5 wt. % |
| | 100.0 wt. % |

The above components 1 to 5 were heated to 50° C. The component 6 was added to the mixture under agitating with a homomixer at 6000 rpm and then the component 7 heated to 50° C. was added slowly to the mixture to obtain a W/O emulsion.

100 parts by weight of the obtained emulsion. was dispersed in 40 parts by weight of a 5% aqueous solution of polyoxyethylene sorbitan monooleate. The dispersion was emulsified again with T. K. Homo Mixer at 80° C. to obtain a cleansing lotion comprising essentially the W/O/W type multiple emulsion.

EXAMPLE 6

12,000 units of insulin was dissolved in 8 ml of 0.1N hydrochloric acid to obtain an aqueous insulin solution.

Separately, 1.5 g of a polyglycerol polyricinolate was dissolved in 30 ml of salad oil. The aqueous solution containing insulin was added dropwise to the latter solution over 3 min in an ultrasonic generator to obtain a W/O emulsion.

This emulsion was added dropwise to 100 ml of a 2% aqueous polyoxyethylene fatty acid ester solution and the mixture was emulsified again with the same ultrasonic generator for 5 min to obtain 136 ml of an insulin-containing W/O/W type multiple emulsion.

EXAMPLE 7

140,000 units of insulin was dissolved in 120 ml of 0.1N hydrochloric acid solution to obtain an aqueous solution containing insulin.

Separately, 10 g of a polyglycerol polyricinolate was dissolved in 200 ml of soybean oil. The aqueous solution containing insulin was added dropwise to the latter solution and the mixture was emulsified in a high-pressure emulsifying device for 10 min to obtain a W/O emulsion.

This emulsion was added dropwise to 900 ml of a 1% aqueous solution of a polyoxyethylene monostearate ester and the mixture was emulsified again in the same device for 15 min to obtain 1340 ml of a W/O/W type multiple emulsion.

EXAMPLE 8

| 1. Inner aqueous phase: | |
| --- | --- |
| maltose | 0.19 g |
| triethanolamine | 0.03 g |
| distilled water | 18 g |
| 2. oil phase: | |
| polyglycerol polyricinolate | 2 g |
| soybean lecithin | 0.07 g |
| olive oil | 2.5 g |
| stearic acid | 0.63 g |
| predonisolone (0.1 wt. %) | 0.05 g |
| 3. outer aqueous phase: | |
| Pluronic F-68 | 0.12 g |
| sucrose monolaurate | 0.06 g |
| triethanolamine | 0.06 g |
| distilled water | 22.4 g |

The mixture 1 was added slowly to the mixture under agitating with a homomixer at 6000 rpm to obtain a W/O emulsion.

The obtained emulsion was dispersed in the mixture 3 and emulsified again with the homomixer to obtain a salve comprising essentially the W/O/W type multiple emulsion.

What is claimed is:

1. A process for producing a W/O/W type multiple emulsion for the production of medicines and cosmetics, comprising the steps of:
    (a) adding an emulsifying amount of polyglycerol polyrincinoleate to an oil phase;
    (b) forming a W/O emulsion by adding an aqueous phase to the product obtained in step (a);
    (c) forming the W/O/W emulsion by adding said W/O emulsion obtained by step (b) to an outer aqueous phase;
    (d) including a medicine or cosmetic within the W/O/W emulsion.

2. A process for producing a W/O/W type multiple emulsion for the production of medicines and cosmetics, comprising the steps of:
    (a) adding an emulsifying amount of polyglycerol polyricinoleate to an aqueous phase;
    (b) forming a W/O emulsion by adding the product obtained by step (a) to an oil phase;
    (c) forming the W/O/W emulsion by adding said W/O emulsion obtained by step (b) to an outer aqueous phase.

3. A process for producing a W/O/W type multiple emulsion for the production of medicines and cosmetics, comprising the steps of:
    (a) forming a W/O emulsion by adding an aqueous phase to an oil phase;
    (b) adding an emulsifying amount of polyglycerol polyricinoleate to an outer aqueous phase;
    (c) forming the W/O/W emulsion by adding said W/O emulsion obtained by step (a) to the product obtained by step (b).

* * * * *